United States Patent [19]

Nimni

[11] Patent Number: 5,104,405
[45] Date of Patent: Apr. 14, 1992

[54] PROCESS FOR IMPROVING THE BIOSTABILITY OF TISSUE IMPLANT DEVICES AND BIOPROSTHETIC IMPLANTS SO PRODUCED

[75] Inventor: Marcel E. Nimni, Santa Monica, Calif.

[73] Assignee: The University of Southern California, Los Angeles, Calif.

[21] Appl. No.: 659,789

[22] Filed: Feb. 21, 1991

[51] Int. Cl.$^5$ .............................................. A61F 2/24
[52] U.S. Cl. .......................................... 623/2; 623/66
[58] Field of Search ...................................... 623/2, 66

[56] References Cited

U.S. PATENT DOCUMENTS 5,002,566 3/1991 Carpentier et al. ...................... 623/2

OTHER PUBLICATIONS

"Inhibition of Ectopic Calcification of Glutaraldehyde Cross-linked Collagen and Collagenous Tissues by a Covalently Bound Diphosphonate (APD)"; Marcel E. Nimni, et al.

"Covalent Binding of Aminopropanehydroxydiphosphonate to Glutaraldehyde Residues in Pericardial Bioprosthetic Tissue: Stablity and Calcification Inhibition Studies", C. L. Webb, et al, Experimental and Molecular Pathology 50, 291-302 (1989).

"Inhibition of Bioprosthetic Heart Valve Calcification with Aminodiphosphonate Covalently Bound to Residual Aldehyde Groups", C. L. Webb, et al; Ann. Thorac Surg. 46: 309-316, Sep. 1988.

"Controlled-Release Drug Delivery of Diphosphonates to Inhibit Bioprosthetic Heart Valve Calcification: Release Rate Modulation with Silicone Matrices via Drug Solubility and Membrane Coating" (Apr. 1987) G. Golomb, et al; Journal of Pharmaceutical Sciences, vol. 76, No. 4.

"Inhibition of Bioprosthetic Heart Valve Calcification by Sustained Local Delivery of Ca and Na Diphosphonate via Controlled Release Matrices"; Gershon Golomb, et al; vol. XXXII Trans. Am. Soc. Artif Intern Organs 1986; pp. 587-590.

"The Role of Glutaraldehyde-Induced Cross-links in Calcification of Bovine Pericardium Used in Cardiac Valve Bioprostheses"; Gershon Golomb, et al; Nov. 1986.

Information from the Claims/U.S. Patents Database Nimni Patents.

"Prevention of Calcification of Bioprosthetic Heart Valve Leaflets by $Ca^{2+}$ Diphosphonate Pretreatment"; T. P. Johnson, et al; Journal of Pharmaceutical Sciences vol. 77, No. 9, Sep. 1988 pp. 740-744.

"The Cross-Linking and Structure Modification of the Collagen Matrix in the Design of Cardiovascular Prosthesis"; Marcel E. Nimni; Journal of Cardiac Surgery 3:523-533; Dec. 1988.

"Biochemical Differences Between Dystrophic Calcification of Cross-linked Collagen Implants and Mineralization During Bone Induction" Calcif Tissue Int (1988) 42: 313-320.

Primary Examiner—David Isabella
Assistant Examiner—Debra S. Brittingham
Attorney, Agent, or Firm—Poms, Smith, Lande & Rose

[57] ABSTRACT

Processes are disclosed for improving the biostability of tissue implant devices. The processes comprise methods for treating harvested tissue with calcification inhibitor, tissue crosslinking reagent, and reagents capable of forming additional tissue reaction sites providing bioprosthetic devices having enhanced amounts of tissue bound calcification inhibitor. After long-term implantation, the treated tissue remains calcification free and exhibits a high degree of physical stability which minimizes the risk of mechanical failure.

22 Claims, 1 Drawing Sheet

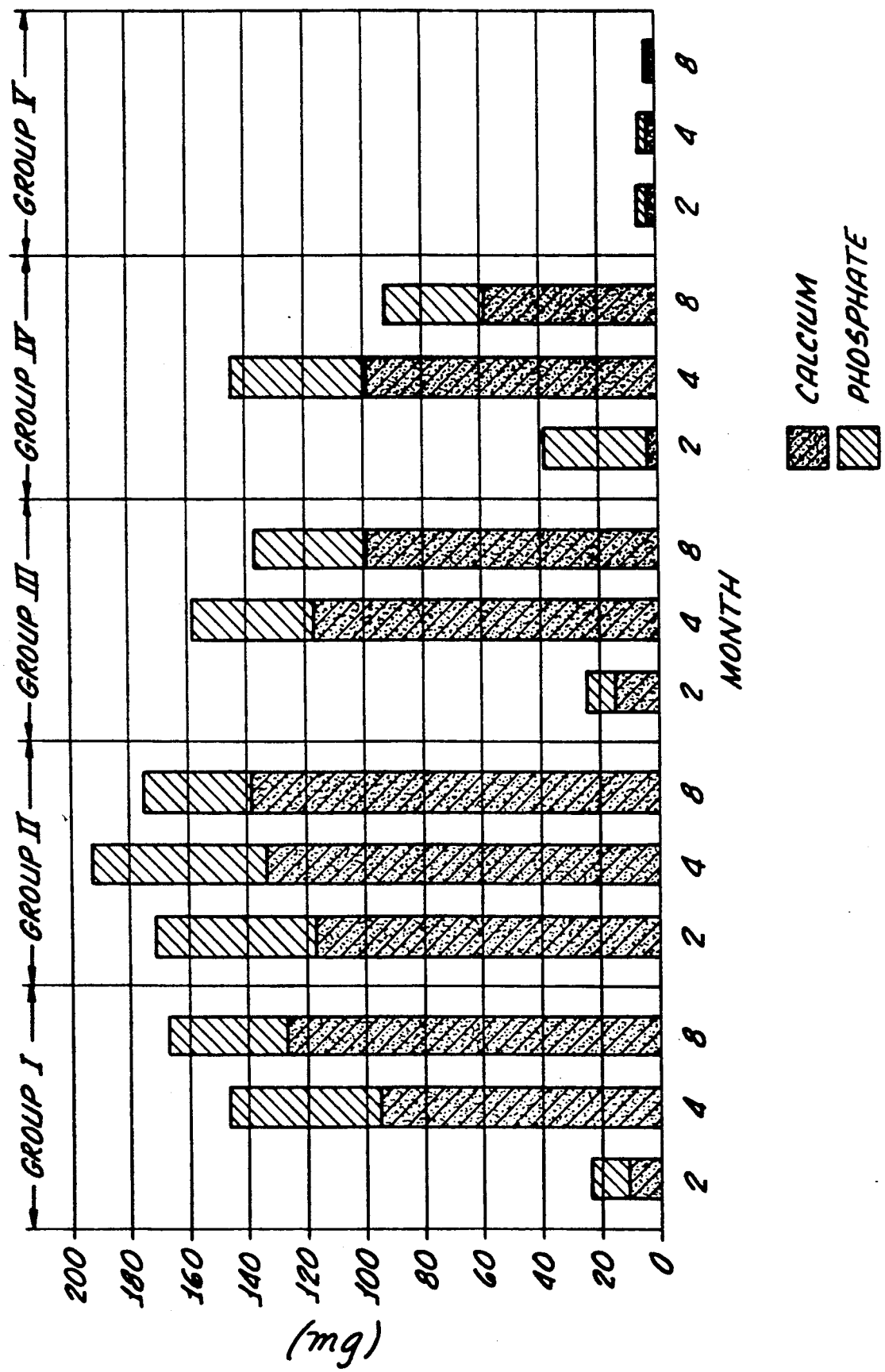

PROCESS FOR IMPROVING THE BIOSTABILITY OF TISSUE IMPLANT DEVICES AND BIOPROSTHETIC IMPLANTS SO PRODUCED

FIELD OF THE INVENTION

The present invention relates in general to tissue bioprosthetic devices and methods for treating tissue prior to its utilization as a bioprosthetic device. In particular, the present invention is directed to methods for treating tissue to provide bioprosthetic devices which are suitable for long term implantation without severe calcification and loss of physical and chemical stability.

BACKGROUND OF THE INVENTION

Tissue harvested from a variety of organisms has found wide spread use in the fabrication of bioprosthetic devices for implanting in both humans and animals. Most notably, prosthetic heart valves fabricated from either mature bovine pericardium or porcine heart valves are important in the management of valvular heart disease. Additionally, animal tissue implant technology has been applied with various degrees of success to other prosthetic devices such as skin, tendons, ligaments, pericardial patches, vascular tissues and collagen implants. Collagen is the most prevalent protein found in these prosthetic devices and the technology of tissue implant devices centers on the chemistry of this protein.

Typically, bioprosthetic devices prepared from harvested tissue are pretreated before the implant procedure with a protein cross-linking reagent. This chemical cross-linking treatment substantially decreases the tendency of the collagenous animal tissue to biodegrade when implanted in a recipient. The increased biostability of the tissue is attributed to a three dimensional cross-linked proteinaceous tissue network having enhanded physical and chemical stability. The cross-linking also decreases the rate of bioprosthetic immunological implant rejections which are caused by anaphylactic reactions to the foreign harvested tissue.

The most universally accepted protein cross-linking agent utilized in connection with pretreating tissue prosthetic devices is glutaraldehyde. Other aldehydes, for example formaldehyde, have also been studied for their usefulness in providing added stability to harvested tissue. However, these aldehydes are less efficient than glutaraldehyde in generating chemically, biologically, and thermally stable cross-links. In general, glutaraldehyde treated tissue exhibits viscoelastic properties which are very close to that of native collagen fibrils.

While cross-linking tissue increases the biological stability and decreases the immunological response of the bioprosthetic implant, an excessive amount of cross-linking will cause a significant loss of the natural tissue flexibility with a corresponding change in the viscoelastic properties. Highly cross-linked tissue will thus become brittle after prolonged periods of implantation and lose varying amounts of their functional advantage. Additionally, the cross-linking treatment itself has some damaging effects on the quality and the texture of the tissue implant. In particular, during the cross-linking process the tissue swells which may result in cell rupture. Tissue damage can also result from exposure to low pH solutions during various treatment steps. Another major and common problem associated with tissue bioprosthetic implants cross-linked with glutaraldehyde is the formation of calcium phosphate crystalline deposits on the altered tissue. This phenomenon, known as calcification, nearly always results in some degree of tearing and stiffening of tissue which has been treated with cross-linking agents. In connection with this problem, calcification is the most frequent cause of the clinical failure of bioprosthetic heart valves fabricated from glutaraldehyde pretreated porcine aortic valves or bovine pericardium.

While increased glutaraldehyde uptake by harvested tissue increases the tissue's biological stability, the degree of tissue calcification is enhanced. See *The Role of Glutaraldehyde-Induced Cross-links in Calcification of Bovine Pericardium Used in Cardiac Valve Bioprostheses*, Golomb et al, Am. J. Pathol. 127, 122–130 (1987). Also see *Biochemical Differences Between Dystrophic Calcification of Crosslinked Collagen Implants and Mineralization During Bone Induction*, Nimni et al., Calcif. Tissue Int. (1988) 42, 313–320. Thus, decreasing the amount of cross-linking, will decrease the degree of calcification yet provide bioprosthetic tissue with limited utility because it is not biologically stable.

One approach to the problem of maintaining a physically stable yet calcification-free tissue bioprosthetic implant device is to utilize calcification inhibitors in connection with pretreating the harvested tissue. For example, U.S. Pat. No. 4,378,224 discloses covalently binding calcification inhibitors to the animal tissue during a glutaraldehyde pretreatment procedure. The process for covalently binding calcification inhibitors to the tissue requires first cross-linking the tissue with a cross-linking reagent to physically stabilize the tissue and prevent tissue swelling. Then, a calcification inhibitor is covalently bonded to residual aldehyde groups following an aldehyde cross-linking reaction; the amount of calcification inhibitor bound to the tissue being dependent upon the availability of unreacted aldehyde functionalities. This approach results in calcification-free bioprosthetic tissue implants during the first three months of implantation. However, recent long term animal model studies indicate the this pretreatment procedure merely prolongs the period in which the tissue remains calcification-free. Because this procedure does not prevent long term calcification, bioprosthetic tissue treated in this manner will eventually calcify.

Other approaches to the problem of providing calcification-free bioprosthetic devices include administering calcification inhibitors to the recipient of the implant. For example, systemic administration of ethanehydroxydiphosphonate completely inhibits the calcification of bioprosthetic heart valve tissue. However, there are severe adverse side effects associated with this approach which include irreversible bone growth inhibition and the disruption of normal bone morphology.

Yet another approach to the use of calcium inhibitors involves providing controlled release matrices for delivering a selected calcium inhibitor locally to the site of the animal tissue implant. For example, a controlled release matrix, prepared from silicone rubber and containing a diphosphonate, has been incorporated into the sewing ring of a bioprosthetic heart valve. See *Inhibition of Bioprosthetic Heart Valve Calcification by Sustained Local Delivery of Ca and Na Diphosphonate via Controlled Release Matrices*, Trans Am Soc Artif Intern Organs, 1986. These controlled release devices are effective for short term control of tissue calcification, but they are not effective for long term use.

Accordingly, it is an object of the present invention to provide a method for pretreating tissue which will render the resulting bioprosthetic tissue suitable for long term use as a implant device.

It is another object of the present invention to provide a process for improving the biostability of harvested tissue in a manner which will simultaneously enhance the physical and chemical stability of the harvested tissue and prevent calcification of the tissue during long term implantation.

It is still another object of the present invention to provide a process for improving the biostability of harvested tissue in a manner which will prevent immunological reactions to the tissue during long term implantation.

It is also an object of the present invention to provide a process for improving the biostability of harvested tissue in a manner which will produce bioprosthetic implant devices having viscoelastic properties similar to native collagen fibrils.

SUMMARY OF THE INVENTION

In a broad aspect, the present invention accomplishes these and other objectives by providing a process which simultaneously improves both the biophysical stability and the calcification resistance of harvested tissue intended for bioprosthetic use by repeatedly loading selected bioprosthetic tissue with calcification inhibitor prior to repeatedly treating the tissue with a cross-linking reagent. However, rather than simply repeating the cross-linking and calcification inhibitor loading the process of the present invention also provides for enhancing the number of reactive sites on the tissue by activating tissue functional groups and binding additional reactive groups to the activated functionalities with bridging agents. Unlike prior art bioprosthetic tissue, tissue treated according to the process of the present invention has sufficiently large amounts of bound calcification inhibitor to prevent calcification of the tissue during long term implantations. However, even though the tissue is repeatedly subjected to cross-linking reagents, the viscoelastic properties of the bioprosthetic tissue of the present invention are much like those of native collagen and remain stable over extended periods of time, greatly enhancing the long term operability of the implants.

Moreover, tissue treated according to the process of the present invention is not physically damaged by cell ruptures or excessive swelling. Because the various process steps are carried out in solutions of high solute concentration which are hypertonic with respect to physiological fluids and prevent the osmotic flow of excess fluids into the tissue cells, the process of the present invention prevents excessive tissue swelling.

More particularly, the present invention provides a process for enhancing the biostability and calcification resistance of bioprosthetic tissue through the steps of loading harvested tissue with a calcification inhibitor; treating the calcification inhibitor loaded tissue with a tissue cross-linking reagent; loading the cross-linking reagent treated tissue with at least one bridging reagent; binding the bridging reagent to the bridging reagent loaded tissue; loading the bridging reagent bound tissue with calcification inhibitor; and treating the calcification inhibitor loaded bridging reagent bound tissue with a tissue cross-linking reagent.

Preferably, the tissue is harvested from animal sources such as porcine heart valves and bovine pericardium, however, other animal and synthetic sources can also be utilized. Similarly, a variety of suitable calcification inhibitors have utility in the practice of the present invention, however, 3-aminopropane-1-hydroxy-1,1-diphosphonate (3-APD) is preferred.

Glutaraldehyde is the preferred cross-linking reagent utilized in the steps requiring reactions with amino functionalities. Additionally, bridging reagents which enhance the number of available sites for both cross-linking tissue and binding calcification inhibitor are preferably dialkylamines such as hexanediamine.

The various steps of the present invention are accomplished by simply immersing the tissue in aqueous solutions which incorporate the selected reagents Actual immersion times and reagent concentrations vary according to the choice of tissue.

As a feature of the present invention, a selected number of steps are carried out by immersing the tissue in aqueous hypertonic solutions. These solutions have a high solute content and prevent tissue swelling. For example, when binding the bridging reagent to tissue, it is preferable to immerse the tissue in an aqueous 0.5 molar NaCl solution of 1-ethyl-3-(dimethyl-aminopropyl)carbodiimide HCl. This water soluble carbodiimide is most reactive at lower pH's which can cause tissue damage in the absence of high concentrations of salt.

The present invention provides tissue with increased amounts of bound calcification inhibitor which appear to enhance the long term calcification resistance of the tissue and the long term biostability of the tissue. Because of the critical function of prosthetic heart valves, the present invention finds particular utility in processes for treating porcine heart valves and bovine pericardia.

Further objects and advantages of the process of the present invention, as well as a better understanding thereof, will be afforded to those skilled in the art from a consideration of the following detailed explanation of preferred exemplary embodiments thereof.

BRIEF DESCRIPTION OF THE DRAWING

The FIG. 1 is a bar graph which illustrates the results of calcium and phosphate analyses of five groups of treated tissue samples which were explanted after being implanted in rats for graded lengths of time.

DETAILED DESCRIPTION OF PREFERRED EMBODIMENTS

The present invention provides highly improved and novel methods for binding calcification inhibitors to tissue without damaging the tissue to produce bioprosthetic tissue implants having significantly improved long term biostability. Tissue which has been treated according to the teachings of the present invention has a surprisingly large amount of calcification inhibitor bound to the surface of the tissue and into the interstices of the tissue as well. This represents a significant improvement over methods known in the art in which the amount of calcification inhibitor bound to the animal tissue provides insufficient protection against calcification in long term bioprosthetic tissue implant devices.

The preferred exemplary embodiments of the present invention are primarily intended to be applied to porcine heart valve tissue and bovine pericardium for the production and subsequent use as bioprosthetic heart valve implants. However, those skilled in the art will appreciate that harvested tissue treated according to the methods of the present invention can also originate from animal blood vessels, ligaments, and tendons as well as from laboratory grown and harvested sources. Accordingly, tissue treated according to the methods described herein find utility for such applications as bioprosthetic skin, tendons, ligaments, pericardial patches, vascular tissues and collagen implants.

Tissue which has been treated in accordance with the teachings of the present invention exhibits long term biocompatability in the form of both physical and chemical stability and will not calcify when implanted in recipient organisms. Additionally, the present invention does not damage the tissue during the treatment process. As a result, the bioprosthetic tissue of the present invention has viscoelastic properties which are similar to that of native collagen fibrils. Moreover, these viscoelastic properties are maintained even after the bioprosthetic tissue has been utilized as a bioprosthetic implant for an extended period of time. As an added benefit bioprosthetic tissue produced in accordance with the teachings of the present invention does not elicit anaphylactic reactions in bioprosthetic implant device recipients and thus have improved immunological characteristics and associated long term implant performance.

In its broadest aspect, the present invention provides methods for treating such tissues in which calcification inhibitor is repeatedly loaded into the tissue prior to repeatedly treating the tissue with cross-linking reagent. Additionally, the process of the present invention prevents tissue swelling while optimizing the available sites for binding calcification inhibitor on the tissue without damaging this tissue or degrading its mechanical properties. The process of the present invention provides bioprosthetic tissue implant having a previously unattainable amount of tissue bound calcification inhibitor by binding calcification inhibitor to the tissue during a first treatment with cross-linking reagent and subsequently increasing the amount of available amino groups on the tissue for binding additional calcification inhibitor during a second treatment with a cross-linking reagent. In this respect, the present invention differs from prior art processes in which a calcification inhibitor is merely allowed to react with any residual cross-linking reagent following an initial treatment with a cross-linking reagent.

More particularly, the present invention provides a process for improving the biophysical stability and calcification resistance bioprosthetic of tissue through the following steps. First, harvested tissue is loaded with calcification inhibitor. As previously mentioned, tissue which is particularly useful in the practice of the present invention is collagenous animal tissue harvested from sources such as porcine heart valves and bovine pericardium. Other sources include collagenous rich tissue such as skin, blood vessels, ligaments, tendons and native collagen fibers harvested from suitable organisms. It is generally preferred that the tissue have readily accessible cross-linking sites such a active residual $NH_2$ functionalities on amino acids. Loading is accomplished through simple immersion or soaking of the tissue in a solution or solutions containing the calcification inhibitor of choice.

Preferably, the calcification inhibitor selected is 3-aminopropane-1-hydroxy-1,1-diphosphonate. However, there are a number of calcification inhibitors known in the art which are also suitable for use in practicing the present invention. These known calcification inhibitors include anionic polysaccharides, diphosphonates with active amino or carboxylate groups, phosphoproteins, ionic dyes, and calcium chelators. Particularly useful polysaccharides include sulfated polysaccharides such as chondroitin sulfates, heparins, chitin, chitosan, and hyaluronates. Ionic dyes having calcification inhibition characteristic include alizarin red and methylene blue. Additionally, it is also contemplated as being within the scope of the present invention to use mixtures of various calcification inhibitors where appropriate, though individual agents are preferred for the sake of simplicity.

Next, the calcification inhibitor loaded tissue is treated with tissue cross-linking reagent to provide partially crosslinked tissue having bound calcification inhibitor. As will be discussed in detail, treatment is preferably accomplished through the simple immersion of the loaded tissue in a solution containing, the reagent or reagents of choice. This step serves to cross-link the available sites on the tissue and to bind the calcification inhibitor to the tissue via residual cross-linking reagent. Glutaraldehyde is the preferred cross-linking reagent; however, those skilled in the art will appreciate that formaldehyde, other multifunctional aldehydes, and reagents capable of reacting with active tissue sites can also be utilized in treating the calcification inhibitor loaded tissue When glutaraldehyde is the selected cross-linking reagent, the glutaraldehyde reacts with residual lysine amino functionalities of the tissue to form cross-links which stabilized the tissue against degradation. The glutaraldehyde also serves to bind the calcification inhibitor to the tissue by reacting with amino functionalities present in, for example, the preferred calcification inhibitor 3-aminopropane-1-hydroxy-1,1-diphosphonate.

Optionally, subsequent to treating the calcification inhibitor loaded tissue with tissue cross-linking reagent, the tissue can be rinsed with saline solution to remove excess cross-linking reagent and unbound calcification inhibitor. Preferably, the rinsing is carried out several times by immersing the tissue for graded lengths of time in freshly prepared saline solutions such as aqueous solutions of approximately 0.09% by weight NaCl.

The next step is to load the cross-linking reagent treated tissue with bridging reagent. Loading the treated tissue with a bridging reagent is preferably carried out through immersion in a hypertonic solution which incorporates the bridging reagent. Suitable hypertonic solutions are solutions of inorganic salts or organic compounds having an osmolality which is substantially greater than the osmolality of the physiological fluids found in native collagenous tissue. For example, aqueous 0.5 molar NaCl solutions have an osmolality approximately 3 times that of physiological fluid and are the preferred hypertonic solutions. When tissue is treated in these hypertonic solutions the greater osmolality prevents the flow of liquids into the cells of the tissue where the excess fluid could cause cell walls to rupture and destroy the physical integrity of the tissue. Thus, the use of such hypertonic solutions decreases the degree of tissue swelling and minimizes the amount of tissue damage during the practice of the present invention.

Bridging reagents which are suitable for use in the practice of the present invention are multifunctional compounds capable of attachment to activated carboxyl sites on the tissue. Preferred bridging reagents are difunctional aliphatic amines such a hexanediamine. Other compounds with free terminal amino or carboxyl groups can also be utilized as bridging reagents. Loading the treated tissue of the present invention with a bridging reagent such as hexanediamine results in tissue which, once appropriately activated, has an increased number of sites for binding calcification inhibitor during subsequent treatment with appropriate cross-linking reagents.

After the tissue is loaded with bridging reagent, the next step is to bind the bridging reagent to the bridging reagent loaded tissue. Binding the bridging reagent to the bridging reagent loaded tissue is preferably carried out by immersing the bridging reagent loaded tissue in an aqueous hypertonic solution which incorporates a reagent which is capable of activating proteinaceous tissue. Water soluble carbodiimides are particularly usefully reagents for this step because they remain in aqueous solution throughout the binding reaction and readily react with and activate protein carboxyl groups available in the harvested tissue to bind the bridging reagent. The activated protein carboxyl groups bind with amine and other functionalities to form attachments and extensions to the tissue. Thus, for example, binding hexanediamine bridging reagent to the loaded tissue can be carried out in an aqueous solution of 1-ethyl-3-(-dimethyl-aminoprop-yl)-carbodiimide.HCl, a water soluble carbodiimide, having carboxyl activation properties which are particular suitable for this process. When incorporated in a 0.5 molar NaCl solution at a reduced pH of approximately 4.7 this water soluble carbodiimide effectively binds selected bridging reagent to the tissue. The reduced pH and elevated salt concentration enhances the efficiency of the binding reaction without accompanying damage to tissue.

After binding the bridging reagent to the tissue to provide additional sites for attachment of calcification inhibitor, bridging reagent bound tissue is again loaded with calcification inhibitor. As mentioned previously, the calcification inhibitor can be any calcification inhibitor such as anionic polysaccharides, phosphoproteins, diphosphonates, and other macromolecules which will sterically hinder the accumulation of calcium and phosphate ions on the surface of collagen and/or interfere with crystal growth. Preferably, the calcification inhibitor is 3-aminopropane-1-hydroxy-1-diphosphonate. Similarly, loading of the additional calcification inhibitor is accomplished through simple immersion or soaking in an aqueous solution of calcification inhibitor. Thus, for example, loading calcification inhibitor in the bridging reagent bound tissue can be carried out in a buffered aqueous solution of 2% wt/vol 3-aminopropane-1-hydroxy-1-1-diphosphonate. Preferably the buffer is HEPES in concentrations giving a pH of 7.4. This subsequent loading step provides additional calcification inhibitor to the surface of the treated tissue and to the interstices within the tissue cells for binding at the additional reactive sites provided by the bound bridging reagent from the preceding step.

The next step is to treat the calcification inhibitor loaded bridging reagent bound tissue with tissue cross-linking reagent to bind the loaded calcification inhibitor to the previously bound bridging reagent and to further cross-link the tissue by directly reacting with the bound bridging reagent. As previously discussed, glutaraldehyde is the preferred tissue cross-linking reagent. Those skilled in the art will appreciate, however, that formaldehyde, other multifunctional aldehydes, and reagents capable of reacting with active tissue sites can also be utilized.

Unlike prior art methodologies which enhance calcification inhibition at the expense of desirable physical and mechanical properties, the present invention improves the biostability of bioprosthetic tissue while enhancing the tissue's resistance to calcification. Without wishing to be bound by this theory, it is believed that this previously unattainable result is accomplished by repeatedly loading the tissue with calcification inhibitor and cross-linking the tissue to bind larger amounts of calcification inhibitor to the tissue coupled with the binding of bridging reagents to form additional sites for binding. Moreover, loading the harvested tissue with calcification inhibitor prior to cross-linking allows the calcification inhibitor to bind to the tissue during the cross-linking process rather than simply binding the calcification inhibitor to residual aldehyde functionalities during the subsequent cross-linking reagent treatment. As a result, calcification inhibitor is freely available to react with a substantial amount of cross-linking reagent and to covalently bind to the tissue sites. Additionally, the use of hypertonic aqueous solutions during many of the process steps prevents the swelling and subsequent tissue damage associated with the prior art tissues. The hypertonic solutions utilized also eliminate the necessity of cross-linking the tissue first to maintain a resistance to swelling.

As noted above, collagenous tissue is available from a number of tissue sources including porcine heart valves, bovine pericardium, skin, tendons, ligaments, vascular tissue, and sponges. Additionally, harvested collagen can be solubilized and reconstituted into collagen fibrils. Those skilled in the art will appreciate that the many and various sources and forms of collagen have different surface areas, tissue morphology, and amino acid populations. In view of this, collagenous tissue, depending upon its source, necessarily has a variety of degrees of reactivity toward cross-linking reagents and carbodiimides. Accordingly, various reagent solutions having reagent concentrations which are suitable for the type of selected tissue should be utilized and the period of time required for each step may vary within the scope of present invention. For example, tissue having a high tendency to calcify, such as bovine pericardium, may require longer periods of time for loading calcification inhibitors and treating the calcification inhibitor loaded tissue. Some tissues saturate with calcification inhibitor within 1 hour, while others saturate more slowly and require up to 24 hours.

The following non-limiting examples illustrate the principles of the present invention. Example I is directed to the production of bioprosthetic tissue implants form harvested porcine aortic heart valves. The process enhances the porcine heart valves' resistance to calcification while improving their biostability and long term functional properties. As noted above, the specified solution concentrations and associated periods of time are adapted for porcine heart valves and are exemplary only.

EXAMPLE 1

Process for Treating Porcine Aortic Heart Valves for Subsequent Use as Bioprosthetic Tissue Implant Porcine heart valves were harvested from host porcine organisms and immediately cleaned from adherent fat and loose connective tissue. The cleaned valves were loaded with 3-amino-1-hydroxypropane 1,1 diphosphonic acid (3-APD) by placing them in a buffered aqueous solution having a concentration of about 1% wt/vol 3-APD. The porcine heart valves and the buffered solution were maintained at about 4°-6° C. for a period of approximately 16 hours.

The 3-APD loaded heart valves were treated with glutaraldehyde using a normal pressure cross-linking cycle. This cycle included treating the valves through immersion in an aqueous solution incorporating approximately 2% vol/vol glutaraldehyde for a period of 2 hours. The treated porcine valves were rinsed 3 times in an aqueous solution of 0.35% vol/vol glutaraldehyde and finally the porcine heart valves were soaked in an aqueous solution of 0.35% glutaraldehyde for 18 to 20 hours.

In order to remove unbound glutaraldehyde and unbound 3-APD the valves were rinsed 3 times with a normal saline solution (0.9% NaCl), each rinse increasing in time from 1 hour to 4 hours to 24 hours. Next, the porcine heart valves were loaded with hexanediamine by placing the valves in an aqueous 0.5 molar NaCl solution having a concentration of 2% wt/vol hexanediamine for a period of 16 hours. In order to bind the hexanediamine to the porcine heart valves, the valves were placed in an aqueous 0.5 molar NaCl solution buffered to a pH of 4.7 and having a concentration of 2% wt/vol 1-ethyl-3-(dimethylaminopropyl) -carbodiimide.HCl, a water soluble carbodiimide (WSCD). This binding reaction took place over a period of 2 hours. During that time the pH was monitored and maintained at 4.7.

Following the step in which the hexanediamine was bound to activated tissue sites, the porcine heart valves were loaded again with 3-APD by placing the valves in an aqueous solution of 2% vol/vol 3-APD for a period of 16 hours at about 22° C. Next the heart valves were again treated with glutaraldehyde in a step which further cross-links the tissue and binds the 3-APD. This step was accomplished by treating the porcine heart valves with an aqueous saline solution of 2% vol/vol glutaraldehyde for 20 minutes and then rinsing the porcine heart valves 3 times with an aqueous 0.5 molar NaCl solution of 0.35% vol/vol glutaraldehyde. Finally, the porcine heart valves were stored in an aqueous solution of 0.35% vol/vol glutaraldehyde until they were selected for implantation.

The following Example 2 is illustrative of the higher amounts of calcification inhibitor bound to collagen fibrils when the tissue is first loaded with the inhibitor and then treated with cross-linking reagent in accordance with the teaching of the present invention. Additionally, this example illustrates the degree to which bound 3-APD calcification inhibitor varies when different types of collagenous tissue are treated in the same manner.

EXAMPLE 2

Quantitative Evaluation of Bound Calcification Inhibitor

Bovine skin in the form of pepsin soluble type I collagen was obtained from cattle. The standard procedure used to isolate the pepsin soluble type I collagen was modified so that no phosphate buffer was used which would interfere with the determination of bound 3-APD. The final form of the pepsin soluble type I collagen was a sponge-like material in a dry, lyophilized state. Additionally, bovine tendon and bovine pericardia were harvested from cattle and cleaned free of adherent tissue.

Small pieces of fresh tendon, fresh pericardia and water reconstituted sponge were left overnight in an aqueous solution containing 1% wt/vol 3-APD and buffered with 50 molar HEPES to a pH of 7.4 to allow the 3-APD to diffuse into the interstices of the tissue. One set of these samples, designated controls were rinsed briefly 2 times in distilled water and then left in running water for 48 hours.

Another set of these 3-APD loaded samples and a set of sponge which was reconstituted in an aqueous 3-APD solution instead of water were treated with an aqueous 50 molar HEPES solution of 2% vol/vol glutaraldehyde for 24 hours. This set was rinsed briefly 2 times with an aqueous solution of 0.2% vol/vol glutaraldehyde and soaked in an aqueous solution of 0.2% vol/vol glutaraldehyde for 24 hours. Finally, this set was stored in an aqueous 50 molar HEPES at a pH of 7.4 for 2 weeks.

Still another set of 3-APD loaded samples was treated with an aqueous 50 molar HEPES solution containing 1% wt/vol hexanediamine. The hexanediamine was then bound to the sample tissue using 1-ethyl-3-(3 dimethylaminopropyl)-carbodiimide.HCl. This set of samples was treated with an aqueous 50 molar HEPES (30 gm/liter pH=7.4) solution of 2% vol/vol glutaraldehyde for 20 minutes and then washed 2 times with an aqueous solution of 0 2% vol/vol glutaraldehyde. Finally, this set of samples, treated to enhance available sites for binding 3-APD, was soaked in an aqueous 50 molar HEPES solution of 0.2% vol/vol glutaraldehyde.

All of the samples belonging to each of the above described sets were tested for bound phosphorous, a criteria for 3-APD binding, using a standard method consisting of oxidizing phosphite to phosphate and analyzing for phosphate. The following table summarizes the values obtained for bound phosphorous. For all types of collagenous tissue, when the tissue was loaded with 3-APD and then thoroughly rinsed without subsequently treating the tissue with glutaraldehyde, the amount of phosphorous retained after rinsing was nil or negligible. When the tissue was treated with glutaraldehyde following the exposure to 3-APD, the amount of retained phosphorous increased dramatically. Finally, in all instances in which the tissue was further bound with hexanediamine, thus enhancing the number of available amino groups for reaction with glutaraldehyde and binding 3-APD, the amount of retained phosphorous was even higher. In the case in which the lyophilized sponge source of collagen was first reconstituted with an aqueous solution of 3-APD and then bound with hexanediame to enhance the available sites for binding 3-APD and glutaraldehyde, the amount of retained phosphorous is the highest. When the fibrils are very small and the network very open, it is conceivable that the diffusion of 3-APD out of the fibril is faster than the rate of penetration of the cross-linking reagent, glutaraldehyde; therefore, significant binding does not occur. This problem was overcome by reconstituting the collagen fibrils in the presence of 3-APD. Upon transfer of the composite to a solution of glutaraldehyde, fixation of the trapped molecules seemed to almost completely saturate the possible binding sites.

TABLE I

Binding of 3-APD To Reconstituted Collagen and Collagenous Tissues

| Specimen | Treatment | moles APD/mg of dry weight ($\times 10^{-9}$)* | moles APD/ mole of collagen |
|---|---|---|---|
| Tendon | APD (not cross-linked) | 0.2 | — |
| | APD + Glut. | 24.8 ± 2.7 | 2.8 |
| | (APD)n | 55.6 ± 4.8 | 6.1 |
| Pericardia | APD (not cross-linked) | 0 | — |
| | APD + GLut. | 32.4 ± 3.4 | 3.6 |
| | (APD)n | 108.5 + 9.8 | 12.1 |
| Reconstituted Collagen | APD (not cross-linked) | 0.1 | — |
| | APD + Glut. | 9.0 ± 1.3 | 1.0 |
| | (APD)n | 16.5 ± 2.6 | 1.8 |
| Collagen (Reconstituted with APD) | None | 1.9 | 0.2 |
| | +Glut. | 154.5 ± 12.1 | 16.2 |
| | (APD)n | 279.0 ± 18.2 | 29.9 |

*Average of 3 specimens analyzed in duplicate.

It is also of interest that tendon, which contains a population of fibrils which are of a larger diameter than those found in pericardia was found to bind proportionately less 3-APD. Likewise, the reconstituted sponge collagen fibrils are even smaller in diameter and even less phosphorous was retained. However, when the sponge collagen fibrils were reconstituted in 3-APD solution more 3-APD was able to penetrate the open network and remain there during the subsequent steps.

One of the principal features of the bioprosthetic tissue of the present invention is its enhanced resistance to calcification during prolonged implant periods. Example 3 illustrates this enhanced resistance in an animal model which is widely accepted for its suitability in the study of the calcification of bioprosthetic tissue subjected to various treatment processes and implanted for graded lengths of time.

EXAMPLE 3

Calcium and Phosphate Content of Explanted Treated Tissue

Five groups of freshly harvested bovine pericardia tissue samples (Groups I-V) were prepared by cleaning the tissue of loose connective tissue and treating each set using one of five different treatment processes. Group I samples were crosslinked using a standard glutaraldehyde treatment procedure for a period of one week. Group II samples were treated in the same manner as Group I samples, but the glutaraldehyde treatment process was allowed to continue for 2 weeks. Group III samples were treated using a standard glutaraldehyde treatment which was prolonged for a period of 2 years. Group IV samples were first treated with glutaraldehyde using standard glutaraldehyde treatment procedures known in the industry. The samples in this group were then loaded with 3-APD for binding to the tissue via the residual glutaraldehyde. Group V samples were treated according to the process of the present invention in which the samples were first loaded with 3-APD and then treated with glutaraldehyde according to standard tissue cross-linking procedures. The Group V bovine pericardium tissue samples were then bound with hexanediamine by first loading the tissue with hexanediamine and then treating the samples with 1-ethyl-3(3 dimethylaminopropyl)-carbodiimide.HCl to find the diamide to the tissue. Finally, the Group V samples were loaded again with 3-APD and treated again with glutaraldehyde to further cross-link the tissue and bind additional 3-APD to the increased number of amino groups bound to the tissue.

Samples taken from Groups I-V were implanted subcutaneously into 2 month old Long Evans rats and then explanted after 2, 4, and 8 months. At the last time of sacrifice the Long Evans rats were approximately 10 months old, the age at whioh the type of physiological calcification being studied ceases to occur. Explanted tissue samples from each study Group were analyzed for both calcium and phosphate content. The higher the amount of calcium and phosphate found in the samples, the higher the degree of calcification.

The Figure illustrates the results of the calcium and phosphate analysis for each group at the time of explant. Group I tissue samples, which were crosslinked for an insufficient length of time, showed a low level of calcification after 2 months, but by 4 months they began to rapidly calcify. In actuality, calcification was occurring at a normal rate in these implants, but because the of all tissue was not sufficiently cross-linked portions of it were rapidly resorbed. Once the very lightly cross-linked tissue and the uncross-linked tissue was substantially resorbed, the more persistent tissue calcified in the predicted fashion.

Group II tissue, which was crosslinked in a normal fashion rapidly crosslinked after 2 months and continued to calcify with time.

The Group III tissue samples which were stored in a glutaraldehyde solution for 2 years before they were implanted, showed little calcification after 2 months and subsequently became heavily calcified. It is believed that a network of polymerized glutaraldehyde may have formed in these samples with resulting tissue shrinkage. This in turn may have altered the accessibility of Ca and $PO_4$ ions to the collagen, as this protective effect dissipated with time, belated calcification occurred.

Group IV tissue samples which were crosslinked and treated with 3-APD under conditions now known to result in only a limited number of diphosphonate molecules binding to the tissue, showed minimal calcification at 2 months and then rapidly began to calcify.

Group V tissue samples were the only samples which failed to calcify throughout the experimental period. These samples were treated according to the process of the present invention which provided the collage fibrils with enhanced amounts of covalently bound 3-APD.

It is interesting to note that for Groups I-IV the amount of calcium accumulated was greater than the amount of phosphate and the two ions existed in ratios that approximated those found in hydroxyapatite. In the case of Group V, the ratios were reversed due to the insignificant amounts of calcium which accumulated. The higher amounts of phosphate in the Group V samples are associated with 3-APD, not hydroxyapatite. This is particularly important in that hydroxyapatite crystals have a needle-like configuration which is known to mechanically damage bioprosthetic tissue as the tissue fibers bend and slide over the sharp crystals. Thus, the present invention is successful at eliminating this problem in addition to its other benefits.

Examples 2 and 3 above clearly illustrate that collagenous bioprosthetic tissue produced in accordance with the teachings of the present invention exhibits significantly enhanced resistance to long term calcification following implantation. Moreover, this calcification resistance is achieved with improved biomedical properties and resistance to tissue degradation.

Having thus described exemplary embodiments of the present invention, it should be noted by those skilled in the art that the disclosures herein are exemplary only and that alternative, adaptations and modifications may be made within the scope of the present invention.

What is claimed is:

1. A process for improving the biophysical stability and calcification resistance of bioprosthetic tissue, said process comprising the steps of:
    loading harvested tissue with calcification inhibitor;
    treating said loaded tissue with tissue cross-linking reagent;
    loading said treated tissue with bridging reagent;
    binding said bridging reagent to said bridging reagent treated tissue;
    loading said bridging reagent bound treated tissue with calcification inhibitor; and
    treating said calcification inhibitor loaded bridging reagent bound treated tissue with tissue cross-linking reagent.

2. The process of claim 1 wherein said treated tissue is loaded with said bridging reagent by immersing said treated tissue in a hypertonic salt solution incorporating said bridging reagent.

3. The process of claim 1 wherein said bridging reagent is bound to said bridging reagent loaded treated tissue by immersing said tissue in a hypertonic salt solution incorporating a carbodiimide.

4. The process of claim 1 wherein said harvested tissue is collagenous tissue.

5. The process of claim 1 wherein said calcification inhibitor is selected from the group consisting of anionic polysaccharides, diphosponates, and phosphoproteins.

6. The process of claim 1 wherein said calcification inhibitor is 3-aminopropane-1-hydroxy-1,1-diphosphonate.

7. The process of claim 1 wherein said crosslinking reagent is glutaraldehyde.

8. The process of claim 1 wherein said bridging reagent is a dialkylamine.

9. A process for improving the biophysical stability and calcification resistance of bioprosthetic tissue, said process comprising the steps of:
    loading harvested tissue with 3-aminopropane -1-hydroxy-1,1-diphosphonate;
    treating said 3-aminopropane -1-hydroxy-1,1-diphosphonate loaded tissue with glutaraldehyde;
    loading said glutaraldehyde treated tissue with hexanediamine, said loading step performed in an aqueous hypertonic solution of hexanediamine;
    binding said hexanediamine to said hexanediamine loaded tissue in an aqueous hypertonic solution of 1-ethyl-3-(-dimethylaminopropyl)-carbodiimide.HCl;
    loading said hexanediamine bound tissue with aminopropanehydroxydiphosphonate; and
    treating said 3-aminopropane -1-hydroxy-1,1-diphosphonate loaded hexane diamine bound tissue with glutaraldehyde.

10. The process of claim 9 wherein said aqueous hypertonic solution has a concentration of approximately 0.5 molar NaCl.

11. The process of claim 9 wherein said loading of said harvested tissue is carried out in an aqueous solution having a concentration of approximately 1% wt/vol 3-aminopropane-1-hydroxy-1,1-diphosphonate.

12. The process of claim 9 wherein said treating of said 3-aminopropane-1-hydroxy-1,1-diphosphonate loaded tissue is accomplished through the additional steps of:
    immersing said 3-aminopropane -1-hydroxy-1,1-diphosphonate loaded tissue in an aqueous solution incorporating approximately 2% vol/vol glutaraldehyde;
    rinsing said glutaraldehyde treated tissue a plurality of times in an aqueous solution of approximately 0.35% vol/vol glutaraldehyde; and
    soaking said rinsed tissue in an aqueous solution of approximately 0.35% vol/vol glutaraldehyde.

13. The process of claim 9 wherein said aqueous hypertonic solution of hexanediamine has a concentration of approximately 2% wt/vol hexanediamine.

14. The process of claim 9 wherein said aqueous hypertonic solution of 1-ethyl-3-(3-dimethylaminopropyl)-carbodiimide.HCl has a concentration of approximately 2% wt/vol 1-ethyl-3-(3-dimethylaminopropyl)-carbodiimide.HCl.

15. The process of claim 9 wherein said loading of said hexanediamine bound tissue is accomplished in an aqueous solution of approximately 2% by volume 3-aminopropane -1-hydroxy-1,1-diphosphonate for a period of several hours.

16. The process of claim 9 wherein said treating of said 3-aminopropane-1-hydroxy-1,1-diphosphonate loaded hexanediamine bound tissue is accomplished through the additional steps of:
    immersing said 3-aminopropane-1-hydroxy-1,1-diphosphonate loaded hexanediamine bound tissue in an aqueous saline solution of approximately 2% vol/vol glutaraldehyde;
    rinsing said 2% vol/vol glutaraldehyde treated tissue a plurality of times with an aqueous hypertonic solution of approximately 0.35% vol/vol glutaraldehyde; and
    soaking said treated tissue in an aqueous solution of approximately 0.35% vol/vol glutaraldehyde for a prolonged period of time.

17. The process of claim 16 wherein said aqueous hypertonic solution is 0.5 molar NaCl.

18. The process of claim 9 further comprising the additional step of rinsing said glutaraldehyde treated tissue in an aqueous solution of approximately 0.9% NaCl prior to loading said glutaraldehyde treated tissue with hexane-diamine.

19. The process of claim 9 wherein said aqueous hypertonic solution of 1-ethyl-3-(-dimettylaminopropyl)-carbodimide HCl is buffered to a pH of approximately 4.7.

20. A bioprosthetic device having enhanced biophysical stability and calcification resistance, said bioprosthetic device comprising bioprosthetic tissue treated according to the process of claim 9.

21. The bioprosthetic device of claim 20 wherein said bioprosthetic tissue is selected from the group consisting of porcine heart vlaves and bovine pericardia.

22. A process for improving the biophysical stability and calcification resistance of collagenous tissue said process comprising the steps of:
    loading harvested collagenous tissue with 3-aminopropane-1-hydroxy-1,1-diphosphonate through immersion in an aqueous solution incorporating approximately 1% wt/vol of 3-aminopropane -1-hydroxy-1,1-diphosphonate, for a period of approximately 20 hours;

treating said 3-aminopropane-1-hydroxy-1,1-diphosphonate loaded collagenous tissue with an aqueous solution incorporating approximately 2% vol/vol glutaraldehyde for a period of approximately 2 hours;

rinsing said glutaraldehyde treated collagenous tissue a plurality of times in an aqueous solution of approximately 0.35% vol/vol lutaraldehyde;

soaking said rinsed collagenous tissue in an aqueous solution incorporating approximately 0.35% glutaraldehyde;

loading said soaked collagenous tissue with hexanediamine through immersion in an aqueous 0.5 molar NaCl solution of hexanediamine;

binding said loaded hexanediamine to said collagenous tissue through immersion in an aqueous 0.5 molar NaCl solution of 1-ethyl-3-(-dimethylaminopropyl)carbodiimide.HCl buffered to a pH of approximately 4.7;

loading said hexanediamine bound collagenous tissue with 3-aminopropane-1-hydroxy-1,1-diphosphonate through immersion in an aqueous solution of approximately 2% 3-aminopropane-1-hydroxy-1,1-diphosphonate for a period of approximately 20 hours;

treating said 3-aminopropane-1-hydroxy-1,1-diphosphonate loaded hexanediamine bound collagenous tissue with an aqueous saline solution of approximately 2% vol/vol glutaraldehyde for a period of approximately 20 minutes;

rinsing said glutaraldehyde treated collagenous tissue a plurality of times with an aqueous 0.5 molar NaCl solution of approximately 0.35% vol/vol glutaraldehyde; and soaking said rinsed tissue in an aqueous solution of approximately 0.35% vol/vol glutaraldehyde for a prolonged period of time.

* * * * *